United States Patent
Cohen et al.

(10) Patent No.: US 11,311,300 B2
(45) Date of Patent: Apr. 26, 2022

(54) BALLOON ASSEMBLY FOR USE IN A HEMOSTASIS BAND

(71) Applicant: Accumed Radial Systems, LLC, Farmington Hills, MI (US)

(72) Inventors: Mauricio Gabriel Cohen, Miami, FL (US); Joseph R. Korotko, Livonia, MI (US)

(73) Assignee: Accumed Radial Systems, LLC, Farmington Hills, MI (US)

( * ) Notice: Subject to any disclaimer, the term of this patent is extended or adjusted under 35 U.S.C. 154(b) by 713 days.

(21) Appl. No.: 14/452,650

(22) Filed: Aug. 6, 2014

(65) Prior Publication Data

US 2016/0038154 A1 Feb. 11, 2016

Related U.S. Application Data

(63) Continuation-in-part of application No. 14/016,034, filed on Aug. 30, 2013, now abandoned, and a continuation-in-part of application No. 13/769,733, filed on Feb. 18, 2013, said application No. 14/016,034 is a continuation-in-part of application No. 13/769,733, filed on Feb. 18, 2013.

(60) Provisional application No. 61/695,291, filed on Aug. 30, 2012, provisional application No. 61/634,772, filed on Mar. 6, 2012.

(51) Int. Cl.
*A61B 17/135* (2006.01)
*A61B 17/132* (2006.01)
*A61B 17/00* (2006.01)

(52) U.S. Cl.
CPC ........ *A61B 17/135* (2013.01); *A61B 17/1325* (2013.01); *A61B 2017/00902* (2013.01)

(58) Field of Classification Search
CPC ..... A61B 17/12; A61B 17/132; A61B 17/135; A61B 17/1322; A61B 17/1325; A61B 17/1327; A61B 17/1355; A61B 5/02233; A61B 2017/12004; A61B 2017/00902; A61F 5/30
See application file for complete search history.

(56) References Cited

U.S. PATENT DOCUMENTS

| | | | | |
|---|---|---|---|---|
| 5,152,302 | A * | 10/1992 | Fareed | A61F 5/34 128/878 |
| 5,792,173 | A * | 8/1998 | Breen | A61B 17/135 606/1 |
| 2004/0010198 | A1* | 1/2004 | Yamakoshi | A61B 5/02233 600/499 |
| 2004/0098035 | A1* | 5/2004 | Wada | A61B 17/1325 606/201 |

(Continued)

OTHER PUBLICATIONS

Dictionary.com definition of Velcro, accessed on Mar. 15, 2017, <http://www.dictionary.com/browse/velcro>.*

*Primary Examiner* — Mohamed G Gabr
(74) *Attorney, Agent, or Firm* — Carlson, Gaskey & Olds, P.C.

(57) ABSTRACT

A balloon assembly (200) that can be attached to a band assembly (300) to form a hemostasis band (100) used to perform hemostasis on a puncture site (89) of a human being (90). The balloon assembly (200) can include a balloon (210) that provides for being inflated to apply pressure to the puncture site (89), one or more openings (220) that provides for the insertion of the band assembly (300), and an inlet (230) for inflating the balloon (210).

13 Claims, 13 Drawing Sheets

(56) References Cited

U.S. PATENT DOCUMENTS

| | | | |
|---|---|---|---|
| 2010/0179586 A1* | 7/2010 | Ward | A61B 17/1322 606/202 |
| 2013/0237866 A1* | 9/2013 | Cohen | A61B 17/1325 600/502 |
| 2014/0142615 A1* | 5/2014 | Corrigan, Jr. | A61B 17/1325 606/201 |

* cited by examiner

BALLOON ASSEMBLY FOR USE IN A HEMOSTASIS BAND

RELATED APPLICATIONS

This utility patent application claims priority to the following patent applications which are hereby incorporated by reference in their entirety: (1) the provisional patent application titled "FLEXIBLE HOLOGRAM USING ROOM LIGHTS WHICH DETECTS ARTERY PULSATION" (Ser. No. 61/634,772) filed on Mar. 6, 2012; (2) the provisional patent application titled "HEMOSTASIS APPARATUS AND METHOD" (Ser. No. 61/695,291) filed on Aug. 30, 2012; (3) the utility patent application titled "HEMOSTASIS APPARATUS AND METHOD" (Ser. No. 13/769,733) filed on Feb. 18, 2013; and (4) the utility patent application titled "HEMOSTASIS SENSOR AND METHOD OF USE THEREOF" (Ser. No. 14/016,034) filed on Aug. 30, 2013.

BACKGROUND OF THE INVENTION

The invention relates generally to hemostasis. More specifically, the invention is a balloon assembly that can be combined with a band assembly to form a hemostasis band that is used to apply pressure on a puncture site to facilitate hemostasis of the puncture site.

I. Hemostasis

Hemostasis means the "stoppage of bleeding or hemorrhage". Human beings and other animals require the flow of blood to sustain life. Blood loss can be fatal to a patient, but steps taken to stem the loss of blood in a patient can also negatively impact the flow of blood in the patient. The amount of pressure on the puncture site required to perform hemostasis can vary based on the location of the puncture site and the cause of the bleeding.

II. Different Causes of Bleeding

There are many contexts in the providing of healthcare to patients when it is necessary to address bleeding or hemorrhage of a patient. Regardless of the cause of the bleeding, information about the flow of blood through and around the puncture site can be highly useful to providers in the treatment of patients undergoing hemostasis.

A. Bleeding that Results from a Patient Condition

In many instances, bleeding is the result of a medical condition of the patient. Examples of bleeding caused by the medical condition of a patient can include diseases, disorders, injuries, allergies, and other conditions that providers seek to address (collectively "conditions").

B. Bleeding that Results from Medical Treatment

Bleeding can also result from the providing of medical treatment and/or the subjecting of the patient to certain types of diagnostic tests. Whether the healthcare activity is undertaken for the purposes of diagnosis (such as a blood test) or treatment (such as the injection of medicine into the patient), activities performed by health care providers (collectively "treatment") can result in bleeding that must be addressed.

C. Intravascular Catheterizations

Intravascular catheterization includes the catheterization of either the arterial or venous systems for diagnosis or treatment of diseases for all systems and organs of the body, such as cardiovascular, neural (brain), pulmonary (lungs), renal (kidneys) and peripheries. Cardiac catheterization is a subset of intravascular catheterization used to diagnose and treat heart conditions. According the Centers for Disease Control and Prevention, heart disease is the leading cause of death in the United States. Cardiac catheterization involves inserting small tubes ("catheters") into the circulatory system of the patient. Using X-ray guidance and other sensors, information about blood flow and blood pressure is obtained. Dyes can be injected into the circulatory system for the purpose of identifying the existence of obstructions such as atherosclerotic plaque within blood vessels. On the basis of the location and number of obstructions, a treatment plan for the patient is devised. Such a treatment plan can utilize different devices, such as the placement of a stent to maintain vessel patency, specialized medications, and/or surgery.

At the beginning of the catheterization procedure a doctor will puncture the vessel to gain access. After gaining access, the necessary catheters are inserted through the "access site" or "puncture site". At the end of the catheterization procedure and after all the catheters are removed, the puncture site must be properly closed. A conventional bandage is insufficient because an artery will bleed out through the bandage because it cannot apply sufficient pressure. The proper amount of pressure, or force, needs to be applied at the puncture site to stop bleeding. The pressure can be applied manually by a health care professional holding pressure with their hand, or a medical device or apparatus can be used to apply pressure.

Cardiac catheterization and other types of intravascular catheterization are commonly performed through either a puncture site the femoral artery in the groin ("femoral catheterization") or the radial artery in the wrist ("radial catheterization").

1. Femoral Catheterization

Femoral catheterization has traditionally been the more common catheterization because the femoral artery is large and the femoral artery provides a direct route to the heart. However, femoral catheterization can require the patient to lie flat without bending their leg for up to 8 hours during recovery. In some cases, there are bleeding complications with femoral catheterization even when the patient fully complies with the immobility restrictions.

2. Radial Catheterization

Radial catheterization involves a puncture site located on the radial artery. Radial catheterization has many advantages over femoral catheterization, including less bleeding complications, improved outcomes and reduced costs. Unlike with femoral catheterization, radial catheterization does not require the patient to be immobile. Moreover, patients find radial catheterization to be the more comfortable option because they are free to sit up, walk around, and even eat.

III. Prior Art Weaknesses

Hemostasis can literally be a matter of life and death. Yet, the prior art does not provide doctors and other health care providers with the most convenient and effective tools for applying hemostasis to a puncture site.

SUMMARY OF THE INVENTION

The invention relates generally to hemostasis. More specifically, the invention is a balloon assembly that can be combined with a band assembly to form a hemostasis band that is used to apply pressure on a puncture site and assist in achieving hemostasis.

The band assembly can be connected to the balloon assembly by inserting the band assembly into one or more openings in the balloon assembly. The balloon assembly can be positioned appropriately with respect to the band assembly, forming a hemostasis band that can provide pressure on a puncture site. One or more balloons on the balloon assembly can be inflated to apply pressure on the puncture site after the balloon and hemostasis band are properly positioned.

The band assembly and balloon assembly can be implemented in a wide variety of different embodiments that are highly modular and configurable.

BRIEF DESCRIPTION OF THE DRAWINGS

Many features and inventive aspects of (1) the balloon assembly itself, (2) the balloon assembly in conjunction with a band assembly to form a hemostasis band, and (3) a method for using the hemostasis band are disclosed in the Figures described briefly below. However, no patent application can disclose all of the potential embodiments of an invention. In accordance with the provisions of the patent statutes, the principles and modes of operation of the balloon assembly, the band assembly, the aggregate hemostasis band, and the method of use thereof are explained and illustrated in certain preferred embodiments. However, it must be understood that the structures and methods described above may be practiced otherwise than is specifically explained and illustrated without departing from its spirit or scope. Each of the various elements described in the index/glossary of Table 1 below can be implemented in a variety of different ways while still being consistent with the spirit and scope of the invention. For example, a hemostasis band comprised of the balloon assembly and the band assembly can be implemented in far more different ways using far more different components in far more different configurations than what is illustrated in the accompanying figures.

All of the element numbers used in the Figures discussed below are listed and described the index/glossary of element numbers provided as Table 1 below.

DETAILED DESCRIPTION

The invention relates generally to hemostasis. More specifically, the invention is a balloon assembly that can be combined with a band assembly to form a hemostasis band that is used to apply pressure on a puncture site.

I. Overview

Figure 1A:
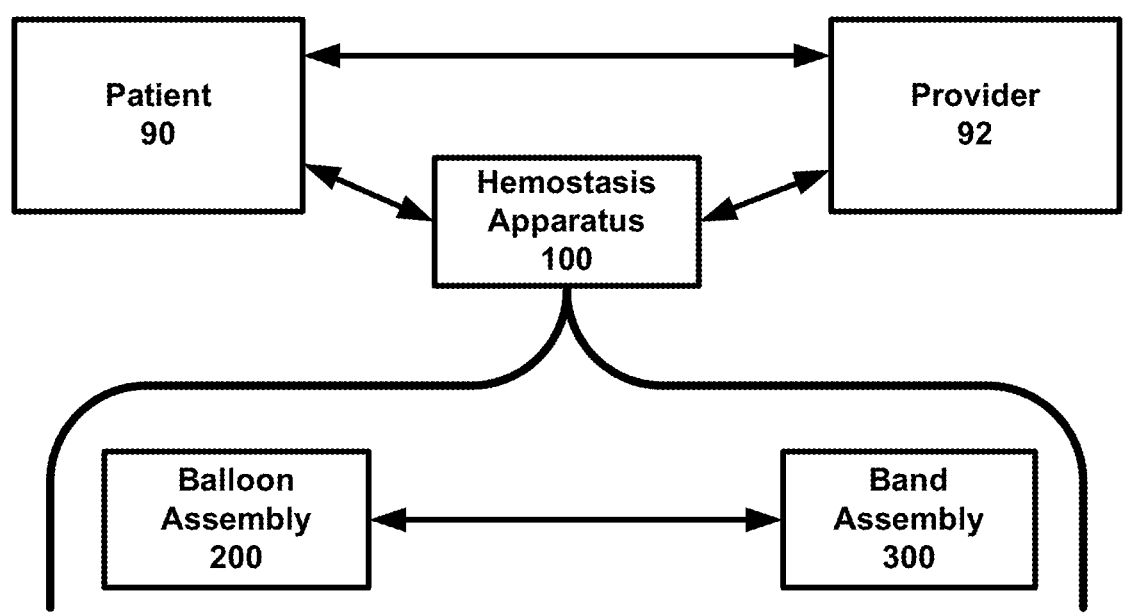
FIG. 1a is a block diagram illustrating an example of interaction between a patient and healthcare provider using a hemostasis band that is comprised of a balloon assembly and a band assembly.
Figure 1B:
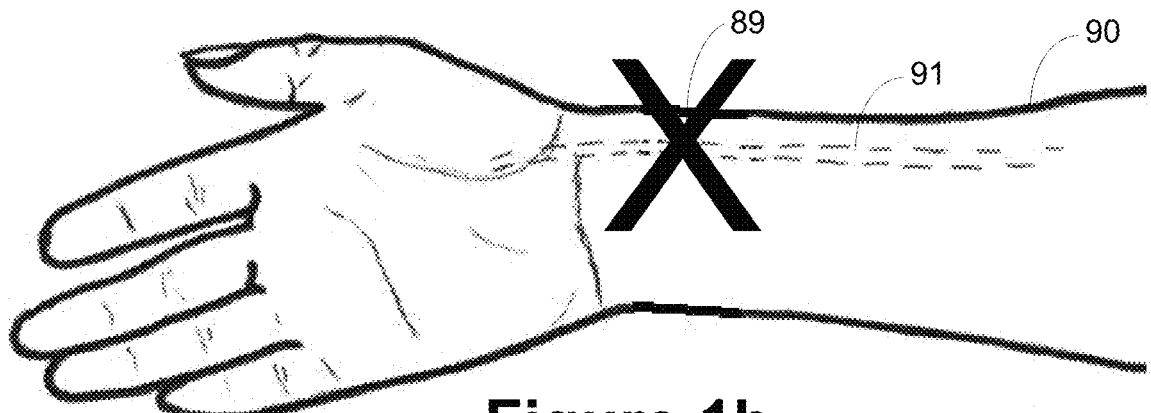
FIG. 1b is an environmental diagram illustrating an example of a puncture site involving the radial artery during a radial catheterization procedure.

FIG. 1a is a block diagram illustrating an example of interaction between a patient 90 and healthcare provider 92 using a hemostasis band 100 that is comprised of a balloon assembly 200 and a band assembly 300. FIG. 1b is an environmental diagram illustrating an example of a puncture site 89 involving the radial artery 91 during a radial catheterization procedure. The hemostasis process involves placing the hemostasis band 100 on the puncture site 89 so that pressure can be placed on the puncture site 89 to stop bleeding at the puncture site 89.

A. Hemostasis Band—Achieving Hemostasis

The hemostasis band 100 is an apparatus that can be secured to the body of the patient 90 while the hemostasis band 100 is used to apply pressure to achieve hemostasis, a process by which the bleeding of the patient 90 is stopped. While the hemostasis band 100 stops bleeding, the body of the patient 90 will naturally close the puncture site 89 incision into the radial artery 91. This "closing" of the puncture site 89 usually takes 1-4 hours depending on patient conditions and medications administered during the catheterization procedure. After the puncture site 89 has closed, the hemostasis band 100 can be removed from the patient 90 and there will be no bleeding.

1. Balloon Assembly

The balloon assembly 200 provides for the functionality of pressurizing the hemostasis band 100 by inflating the balloon assembly 200. The position of the balloon assembly 200 can be moved/adjusted with respect to the band assembly 300. In some embodiments of the balloon assembly 200, it is manufactured separately from the band assembly 300 and the hemostasis band 100 is assembled together by the provider 90 or someone else at the location of the patient 90. In other embodiments, the balloon assembly 200 and band assembly 300 are manufactured, sold, transported, and used as a unit.

In many embodiments of the balloon assembly 200, it is the balloon assembly 200 that is in direct contact with the puncture site 89 during the hemostasis process. In other embodiments, a surface or component in the band assembly 300 can be in direct contact with the puncture site 89 of the patient 90.

2. Band Assembly

The band assembly 300 provides for all functions of the hemostasis band 100 that are unrelated to the inflation/deflation of the balloon assembly 200. Among other functions, the band assembly 300 provides the "band" structure of the hemostasis band 100. The band assembly 300 secures the position of the hemostasis band 100 to the patient 90 even if it is the balloon assembly 200 that is in direct contact with the puncture site 89 of the patient 90.

B. Features/Advantages

The hemostasis band 100 can be implemented with a variety of useful features and attributes.

1. Modularity

The hemostasis band 100 can be comprised of two highly or even fully modular assemblies, the balloon assembly 200 and the band assembly 300. The balloon assembly 200 and the band assembly 300 can be manufactured separately and combined as needed by providers 92. The hemostasis band 100 can be configured to allow a balloon assembly 200 to be used with multiple band assemblies 300, and vice versa.

2. Adjustments

The balloon assembly 200 can be moved to a variety of different positions on the band assembly 300. This flexibility can be utilized before the hemostasis band 100 is secured on the puncture site 89, during the hemostasis process while the band 100 is on the patient 90, after the hemostasis process is complete while the band 100 is on the patient 90, or even after the band 100 has been removed from the patient 90.

3. Transparency

The hemostasis band 100, and its various assemblies and components, can be implemented with a wide variety of different materials. Some embodiments of the band 100 can utilize transparent or at least substantially transparent materials. This can allow providers 92 to see the puncture site 89 even while the hemostasis band 100 is performing hemostasis on the puncture site 89. This visibility can help the provider 92 to avoid the undesirable extremes of too little pressure being applied to the puncture site 89 or too much pressure being applied to the puncture site 89.

C. Process Flow

Figure 1C:
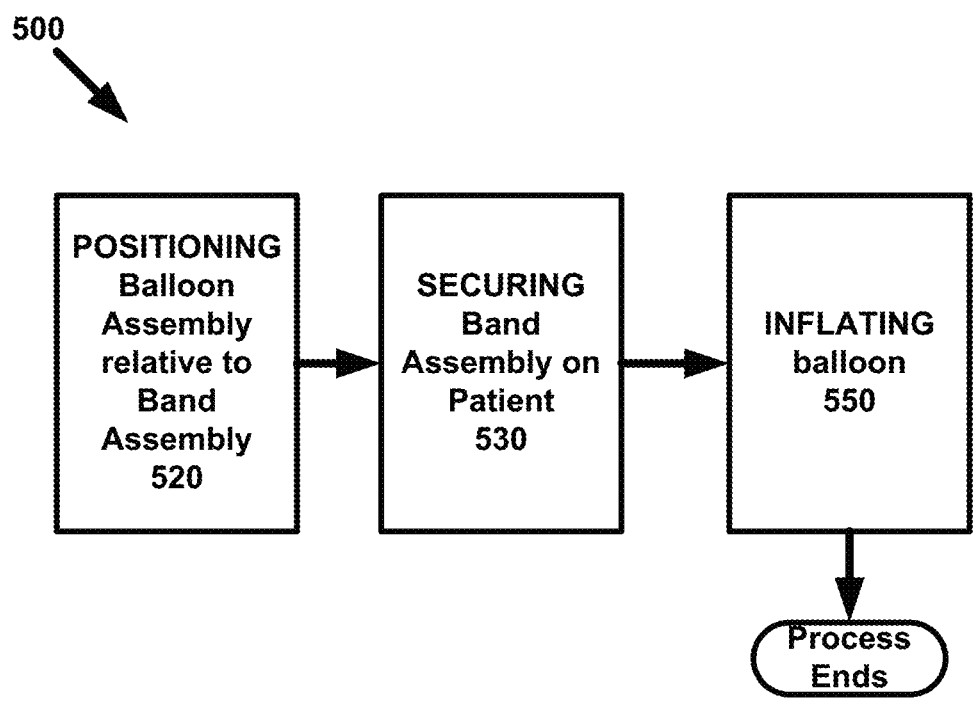
FIG. 1c is a flow chart diagram illustrating an example of a process for utilizing a hemostasis band with a balloon assembly that can be positioned with respect to a band assembly.

FIG. 1c is a flow chart diagram illustrating an example of a process 500 for utilizing a hemostasis band 100 with a balloon assembly 200 that can be positioned with respect to a band assembly 300.

At 520, the balloon assembly 200 is positioned relative to the band assembly 300.

At 540, the band assembly 300 is secured to the body of the patient 90.

At 550, the balloon assembly 200 is inflated. This increases the pressure on the puncture site 89, which results in the process of hemostasis being achieved on the puncture site 89.

II. Balloon Assembly

Figure 2A:
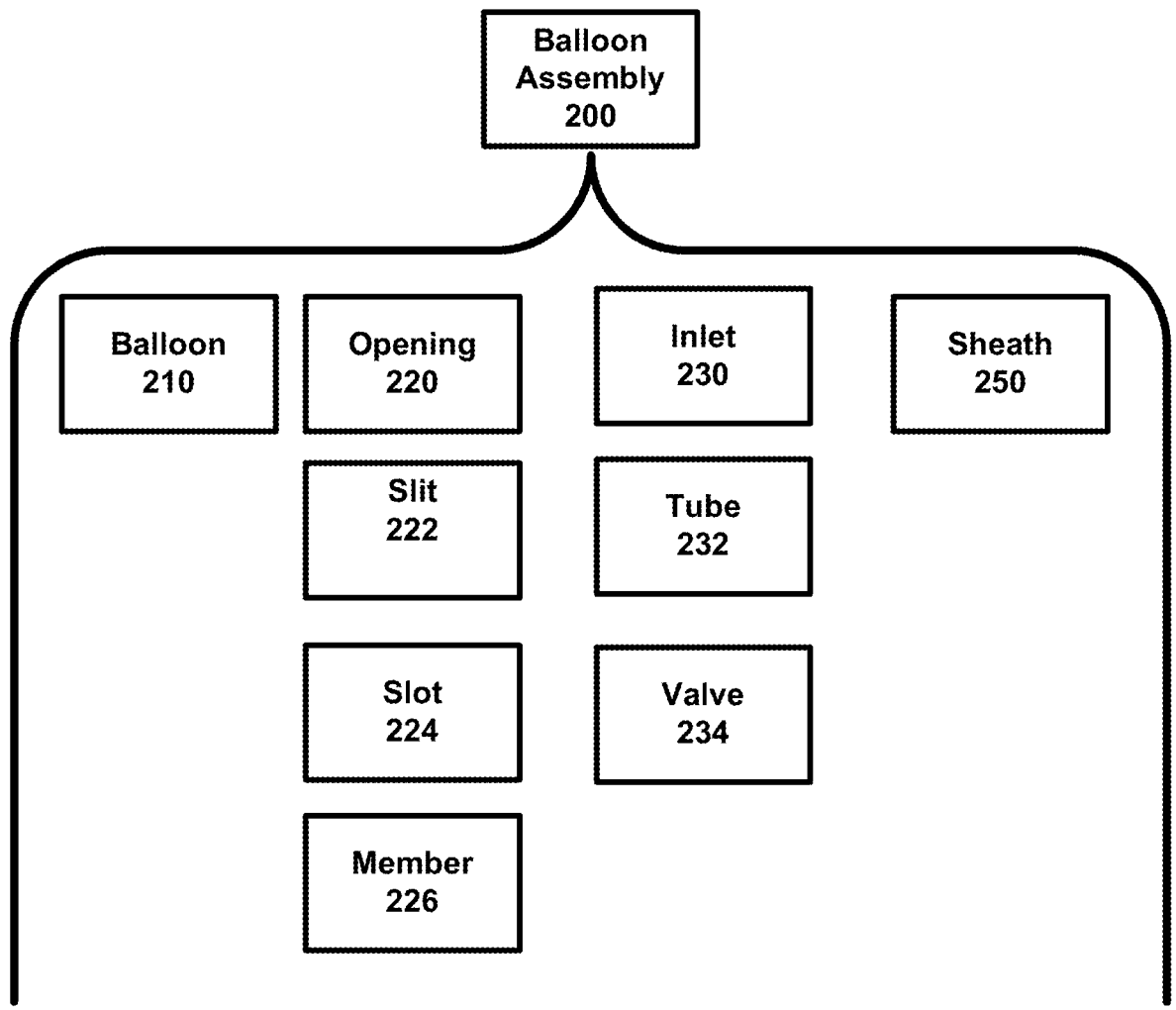
FIG. 2a is a block diagram illustrating an example of different components that can be included as part of a balloon assembly.

FIG. 2a is a block diagram illustrating an example of different components that can be included as part of a balloon assembly 200. All of the elements identified below are also discussed in greater detail in the index/glossary of element numbers provided as Table 1 below.

In the aggregate, the function of the balloon assembly 200 is to allow a provider 90 to apply pressure to the puncture site 89. This can be done by inflating the balloon assembly 200. The balloon assembly 200 will also have the function to adjust the applied pressure as necessary. During the hemostasis process, the pressure in the balloon assembly 200 can be increased or decreased as needed.

A. Balloon

The balloon assembly 200 can include a varying number of balloons 210. In many embodiments, the balloon assembly 200 will include only one balloon 210, but in alternative embodiments, other configurations can be used. The balloon 210 will often be the component of the band 100 that is in direct contact with the puncture site 89, applying pressure over the incision. The pressure stops bleeding while the body naturally closes the incision in the skin and artery The balloons 210 incorporated into the balloon assembly 200 can be comprised in a variety of shapes, sizes, and dimensions. A wide range of materials and manufacturing processes can be used to create the balloons 210 used by the assembly 200.

A balloon 210 can be made by RF (radio frequency) welding two layers of polymer film together. The RF welding creates the seal around the perimeter of the balloon. RF technology can be used on materials that have the correct form of dipolar molecules. The radio frequency excites the molecules imparting energy which causes the material to go from a solid to liquid state. After the RF input is stopped, the material cools back to a solid state creating a weld between the two layers of polymer.

The balloon 210 could be manufactured using a blow molding method. Blow molding is valuable for apparatuses that have a cavity or hollow area. Common examples are bottles, containers or larger polymer structures that are hollow. Some children toys are made using blow molding. Medical devices can also be made using blow molding, such as medical bottles, or containers for blood or bodily fluids. It is envisioned that the balloon 210 component for the band can be made using a blow molding manufacturing method.

The balloon 210 could be manufactured using a dip molding method. A dipping mandrel in the shape of the balloon 210 can be made. The mandrel would be dipped into a vat containing liquid polymer. Some of the polymer would adhere to the mandrel. Repetitive dipping adds layers of polymer. When the desired thickness of balloon has been achieved, it can be removed from the mandrel, thus creating the balloon 210.

Examples of balloons can be seen in FIGS. 2a-2g. If a balloon 210 is neither transparent nor at least semi-transparent, the balloon 210 can include a substantially transparent window 212 (see FIG. 2f) that allows for a provider 90 to see the puncture site 89 under the band 100 while hemostasis is being performed.

B. Opening

Returning to FIG. 2a, the balloon assembly 200 will include an opening 220 through which the band assembly 300 can be positioned. Many embodiments of the balloon assembly 200 will include two or even more openings 220. Openings 220 facilitate the ability of the balloon assembly 200 and the band assembly 300 to be combined into a single hemostasis band 100. Many openings 220 can be characterized as being either slits 222 or slots 224. Examples of openings 220 are illustrated in FIGS. 2a-2f.

1. Slits

Figure 2B:
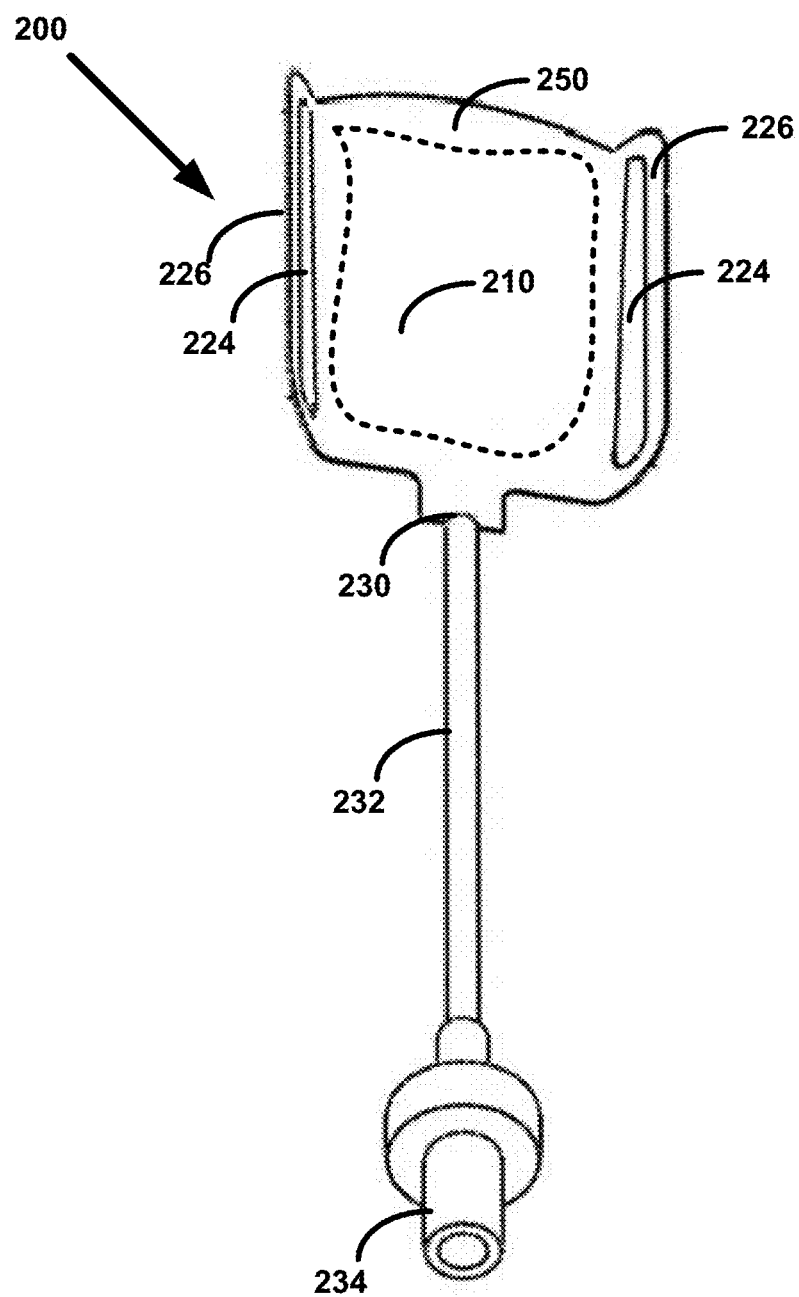
FIG. 2b is a diagram illustrating an example of a top view of a balloon assembly that includes a sheath, a tube, and a valve.
Figure 2C:
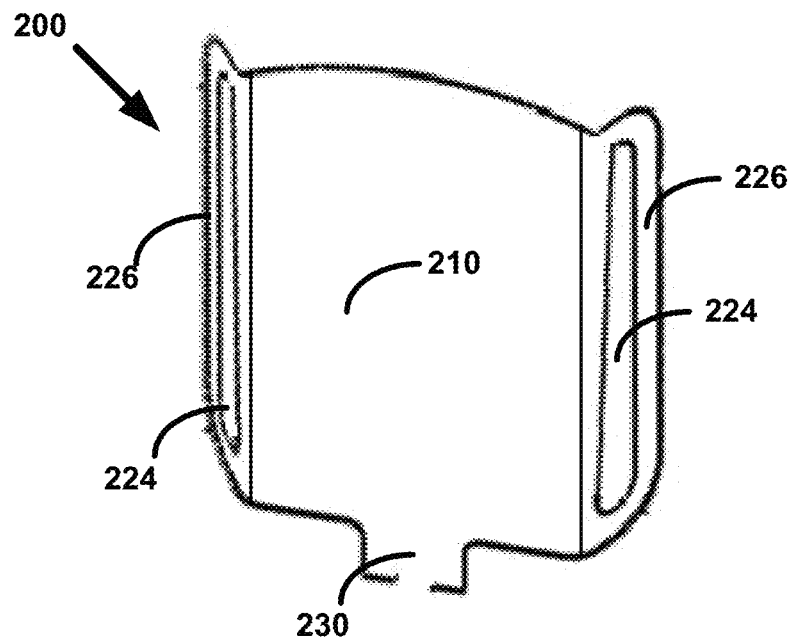
FIG. 2c is a diagram illustrating an example of a top view of a balloon assembly that includes a slot as an opening but does not include a sheath
Figure 2D:
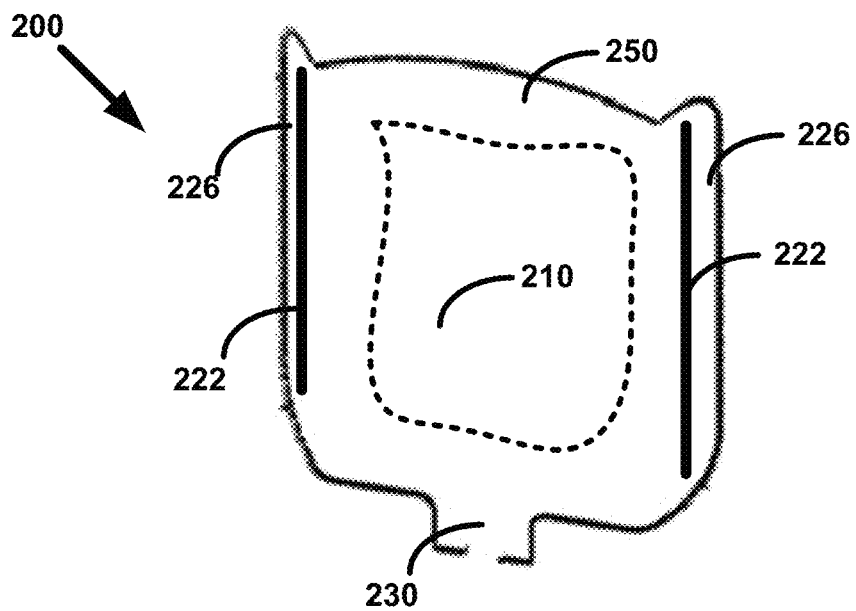
FIG. 2d is a diagram illustrating an example of a top view of a balloon assembly that includes a slit as an opening and a sheath that encloses a balloon.
Figure 2E:
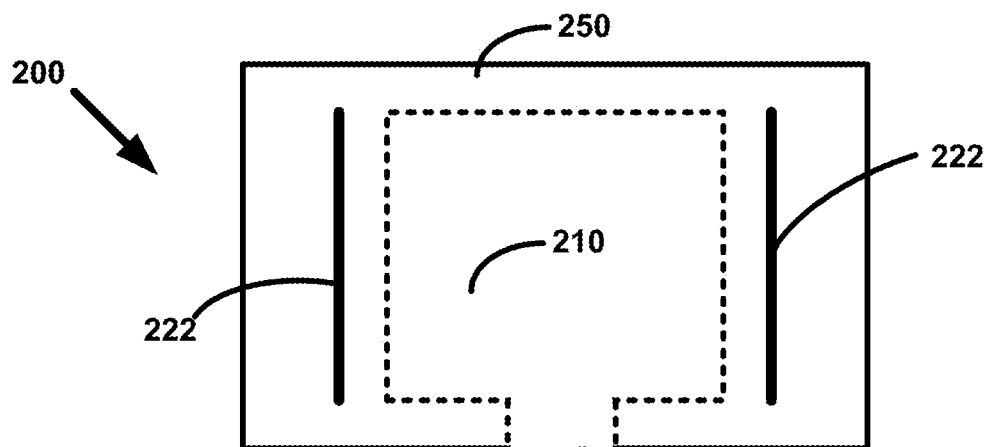
FIG. 2e is a diagram illustrating an example of top view of a balloon assembly that includes a slit as an opening and a sheath that encloses a balloon.

A slit 222 is a narrow cut-like opening in the balloon assembly 200. Analogous to a button hole, such an opening 220 often requires manual prodding to create sufficient open space for the band assembly 300 to be positioned into the opening 220. Examples of slits 222 are illustrated in FIGS. 2a, 2d, and 2e.

2. Slots

Figure 2F:
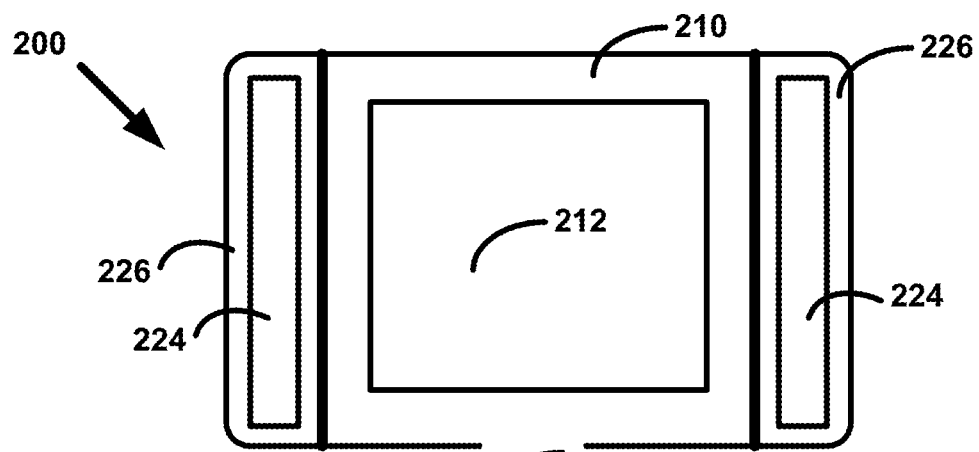
FIG. 2f is a diagram illustrating an example of a top view of a balloon assembly that includes a slot as an opening, a window over the balloon, but does not include a sheath.

A slot 224 is a more substantial opening 224 than a slit 222. A slot 224 does not require manual prodding to create space. Examples of slots 224 are illustrated in FIGS. 2b, 2c, and 2f.

3. Members

The space of an opening 220 is often shaped by a member 226 that is exterior to the opening 220. Such members 226 can be configured in a wide variety of different shapes, sizes, types of materials, etc. Examples of members 226 are illustrated in FIGS. 2a-2d, and 2f.

C. Sheath

Returning to FIG. 2a, the balloon assembly 200 can include a sheath 250 that is used to house the balloon 210, openings 220, and potentially other parts of the balloon assembly 200. The sheath 250 can be comprised of virtually any material used to make the balloon 210 or the members 226. Examples of sheaths 250 are illustrated in FIGS. 2a, 2b, 2d, and 2e.

D. Inlet

Returning to FIG. 2a, the balloon assembly 200 can include an inlet 230 that provides for the inflation and deflation of the balloon 210. Examples of inlets 230 are illustrated and expressly identified in FIGS. 2a-2d.

1. Tube

A tube 232 can make it easier and more convenient to inflate and/or deflate the balloon 210. The tube 232 allows inflation and deflation to take place further away from the body of the patient 90. An example of a tube 232 is illustrated in FIGS. 2a-2b.

2. Valve

A valve 234 can make it easier for the balloon 210 to stay inflated as well as to be deflated. The valve 234 can possess a variety of operating modes such as fully open, fully closed, and a variety of operating states in between.

E. Drawings of Balloon Assembly

FIG. 2b is a diagram illustrating an example of a top view of a balloon assembly 200 that includes a sheath 250, a tube 232, and a valve 234.

FIG. 2c is a diagram illustrating an example of a top view of a balloon assembly 200 that includes a slot 224 as an opening 220 but does not include a sheath 250.

FIG. 2d is a diagram illustrating an example of a top view of a balloon assembly 200 that includes a slit 222 as an opening 220 and a sheath 250 that encloses a balloon 210.

FIG. 2e is a diagram illustrating an example of top view of a balloon assembly 200 that includes a slit 222 as an opening 220 and a sheath 250 that encloses a balloon 210.

FIG. 2f is a diagram illustrating an example of a top view of a balloon assembly 200 that includes a slot 224 as an opening 220 but does not include a sheath 250.

Figure 2G:
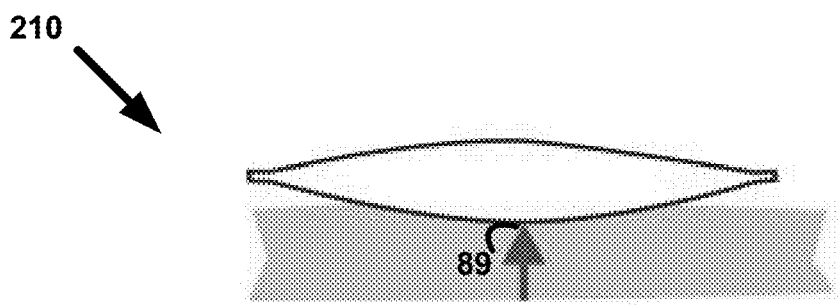
FIG. 2g is a diagram illustrating an example of a side view of a balloon that is inflated over a puncture site.

FIG. 2g is a diagram illustrating an example of a side view of a balloon 210 that is inflated over a puncture site 89.

III. Band Assembly

The band assembly 300 is the portion of the hemostasis band 100 that comprises the band itself (comprised of one more segments 330), as well as providing the structures for securing the hemostasis band 100 onto the patient 90. The band assembly 300 can be implemented in a wide variety of different structures, from a simple elastic band that holds the balloon assembly 200 in place to a complex assembly that includes sensors, electronic communications, computer processors, and other components that may be useful to the hemostasis process, whether directly or indirectly.

Figure 3A:
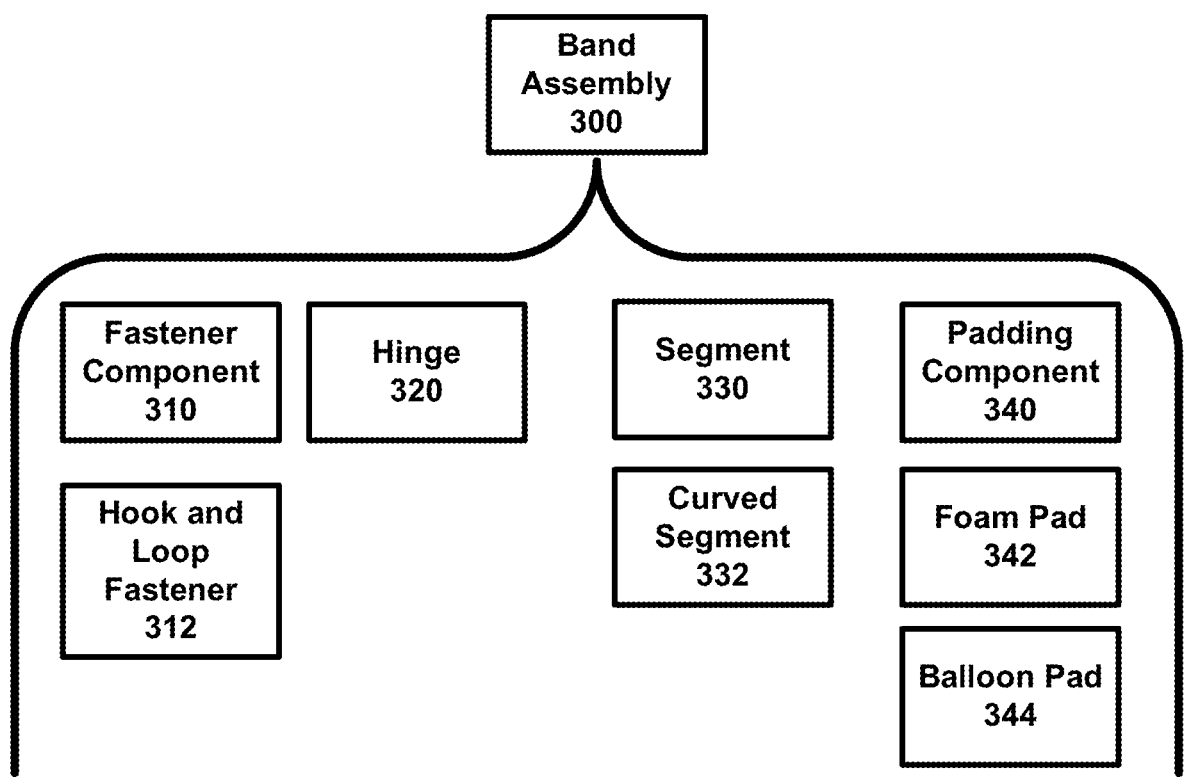
FIG. 3a is a block diagram illustrating an example of different components that can be included as part of the band assembly.

FIG. 3a is a block diagram illustrating an example of different components that can be included as part of the band assembly 300. As illustrated in FIG. 3a, the band assembly 300 can include a fastener component 310, including but not limited to a hook and loop fastener 312 commonly referred to as VELCRO®, a hinge 320 that connects segments 330 of the band 100 together, and padding components 340 such as a foam pad 342 or a balloon pad 344.

The components of the band assembly 300 can be manufactured using injection molding methods or die cut from stock material.

A. Fastener Component

A fastener component 310 is a portion of the band assembly 300 that is used to secure the band assembly 300 on the patient 90. A mechanism or component of the band assembly 300 by which the band assembly 300 and the hemostasis band 100 as a whole, can be secured to the patient 90. Many embodiments of the band assembly 300 will require some type of fastener component 310. In some embodiments of the band assembly 300, the segment 330 of the assembly 300 is an elastic band that serves at its own fastener to the patient 90. In other embodiments, the band assembly 300 will use a snap, button, zipper, adhesive surface, hook and loop fastener 312, or other similar technology to secure two ends of the band assembly 300 together while the balloon assembly 200 is secured to the band assembly 300. Examples of fastener components 310 are illustrated in FIGS. 3a, 3g, and 3h, B. Hinge If a band assembly 300 includes two or more segments 330, one or more hinges 320 can be used to link those segments together. The functionality of the hinge 320 allows one segment 330 to move with respect to another. That movement and positioning can provide for a band 100 being opened and closed. Thus, the hinge 320 can be an important aid in securing the position of the band 100 on the patient 90. Examples of hinges 320 are illustrated in FIGS. 3a, 3d, 3g, and 3h.

In many embodiments of the hinge 320, the hinge 320 will be an actual hinge that includes a hinge pin. In other embodiments, the hinge 320 can implement a "living hinge" concept where the function is equivalent to a hinge without having the express structural components of a hinge.

C. Segment

The band assembly 300 can be comprised of one, two, or even more segments 330 which can also be referred to as "band segments" or "band surfaces". Some embodiments of a band 100 can involve a single segment 330 that could be fashioned with a fastener component 310 on each end (see FIG. 3b) or even a single segment 330 that is an elastic loop (see FIG. 3c). Other embodiments of the band assembly 300 will often involve two or more segments 330 and one or more hinges 320.

Many embodiments of rigid or at least partially rigid segments 330 will involve curved segments 330. Examples of segments 330 can include a flexible elastic band, a strip, a loop, a semi-flexible/semi-rigid band, and a fully rigid band. Segments 330 can serve as the relevant surface of the band assembly 300 that various components are attached to (virtually all of the components of the band assembly 300) as well as the relevant portion of the band assembly 300 that moves within the openings 220 and with respect to the balloon assembly 200. A segment 330 that is curved can be referred to as a curved segment 332.

Segments 330 can be implemented in wide variety of different shapes, sizes, materials, transparency levels, etc.

D. Padding Component

Returning to FIG. 3a, the band assembly 300 can also include as few as zero padding components up to as many padding components 340 that can fit on the various segments 330 of the band 100. Padding components 340 exist for the purpose of the comfort of the patient 90. Examples of padding components 340 can include a foam pad 342 or a balloon pad 344 (i.e. an additional balloon). The pad component and closure mechanism can be manufactured with more than one method. Either could be molded, die cut, rotary die cut or water jet cut. The components would have the same feature regardless of manufacturing method.

E. Band Assembly Drawings

Figure 3B:
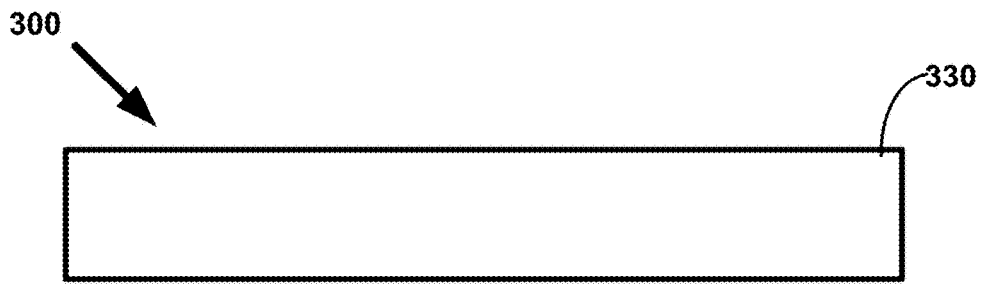
FIG. 3b is a diagram illustrating an example of a top view of a band assembly in the form of a single rectangular strip.

FIG. 3b is a diagram illustrating an example of a top view of a band assembly 300 in the form of a single rectangular strip as the sole segment 330.

Figure 3C:
FIG. 3c is a diagram illustrating an example of a side view of a band assembly in the form of a continuous elastic loop.

FIG. 3c is a diagram illustrating an example of a side view of a band assembly 300 with a single segment 330 in the form of a continuous elastic loop.

Figure 3D:
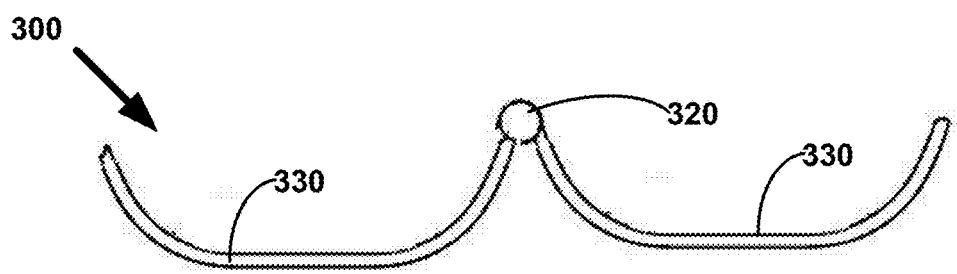
FIG. 3d is a diagram illustrating an example of a side view of a band assembly that includes two segments connected by a hinge.

FIG. 3d is a diagram illustrating an example of a side view of a band assembly 300 that includes two segments 330 connected by a hinge 320.

Figure 3E:
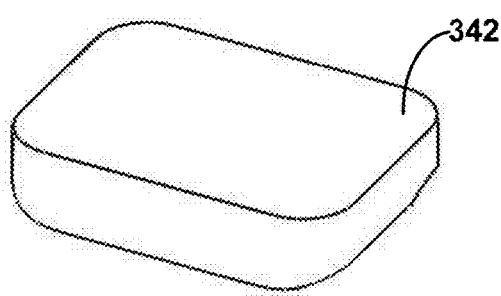
FIG. 3e is a diagram illustrating an example of a perspective view of a foam pad.

FIG. 3e is a diagram illustrating an example of a perspective view of a foam pad 342.

Figure 3F:
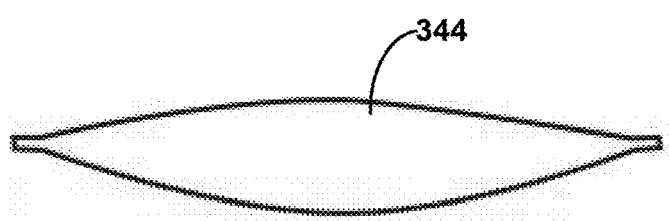
FIG. 3f is a diagram illustrating an example of a perspective view of a balloon pad.
Figure 3G:
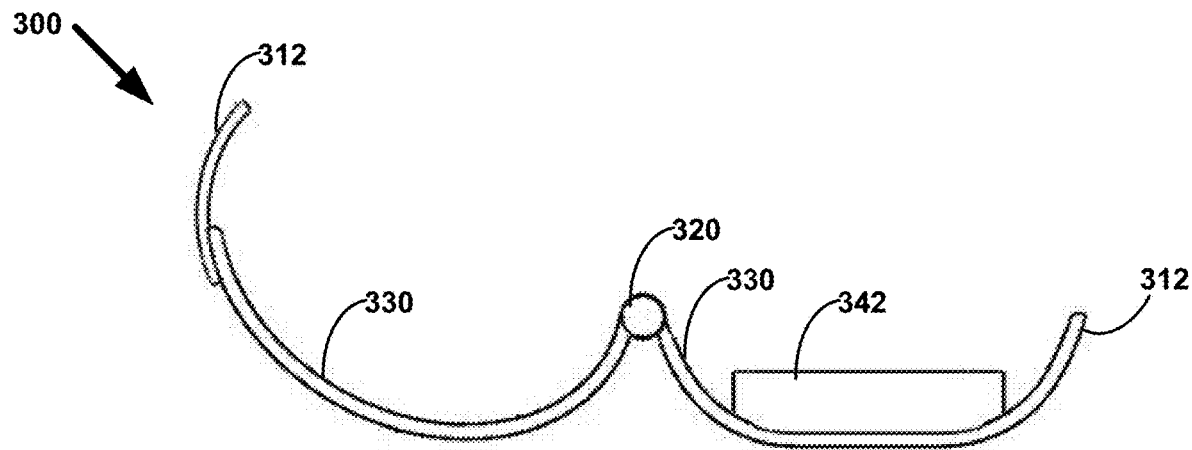
FIG. 3g is a diagram illustrating an example of a side view of a band assembly in an open position.
Figure 3H:
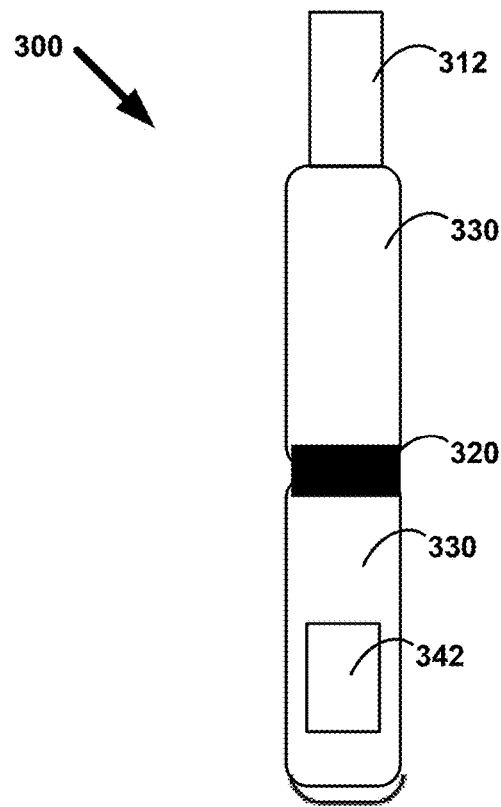
FIG. 3h is a diagram illustrating an example of a top view of a band assembly in an open position.

FIG. 3f is a diagram illustrating an example of a perspective view of a balloon pad 344.

FIG. 3g is a diagram illustrating an example of a side view of a band assembly 300 in an open position.

FIG. 3h is a diagram illustrating an example of a top view of a band assembly 300 in an open position.

IV. Hemostasis Band as a Mechanism for Hemostasis

The hemostasis band 100 can be implemented in a wide variety of different embodiments with utilizing different components, component configurations, materials, geometries, and other attributes. For some embodiments of the band 100, components can be manufactured using injection molding methods or die cut from stock material.

Figure 4A:
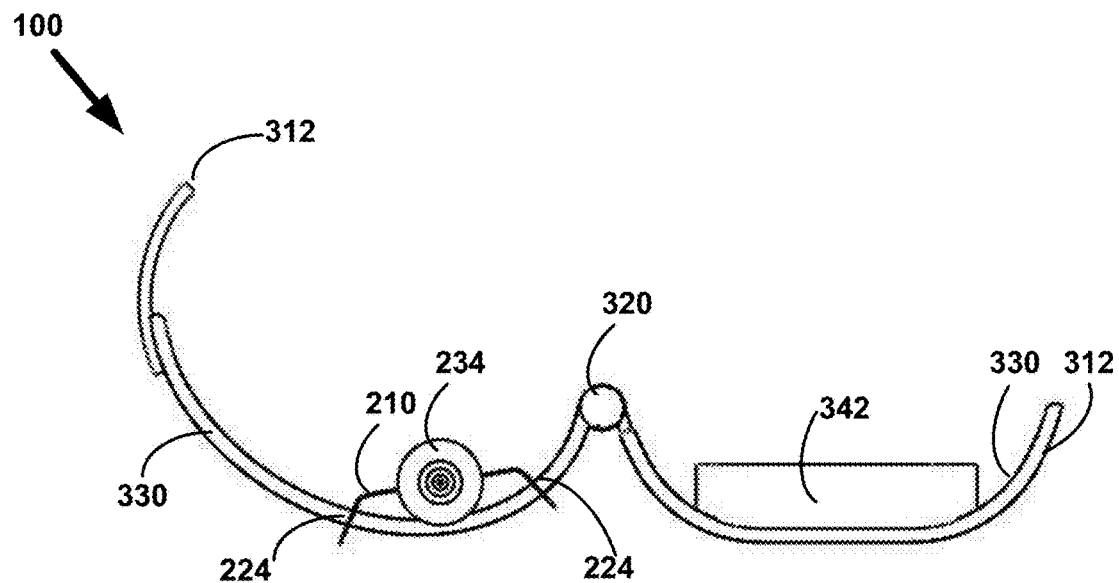
FIG. 4a is a diagram illustrating an example of a side view of a hemostasis band in an open state that is comprised of a balloon assembly and a band assembly

FIG. 4a is a diagram illustrating an example of a side view of a hemostasis band 100 in an open state that is comprised of a balloon assembly 200 and a band assembly 300. In terms of the balloon assembly 200, there is a balloon 210 illustrated with a valve 234. The positions of two slots 224 are also illustrated. The entire balloon assembly 200 is positioned on one segment 330 between the hinge 320 and the fastening component 312 of the band assembly 300. The band assembly 300 includes a hinge 320 connecting two segments 330, a fastening component 312 comprised of two straps of VELCRO® material fixed to those two segments 330. A foam pad 342 is fixed to one of the segments 330.

Figure 4B:
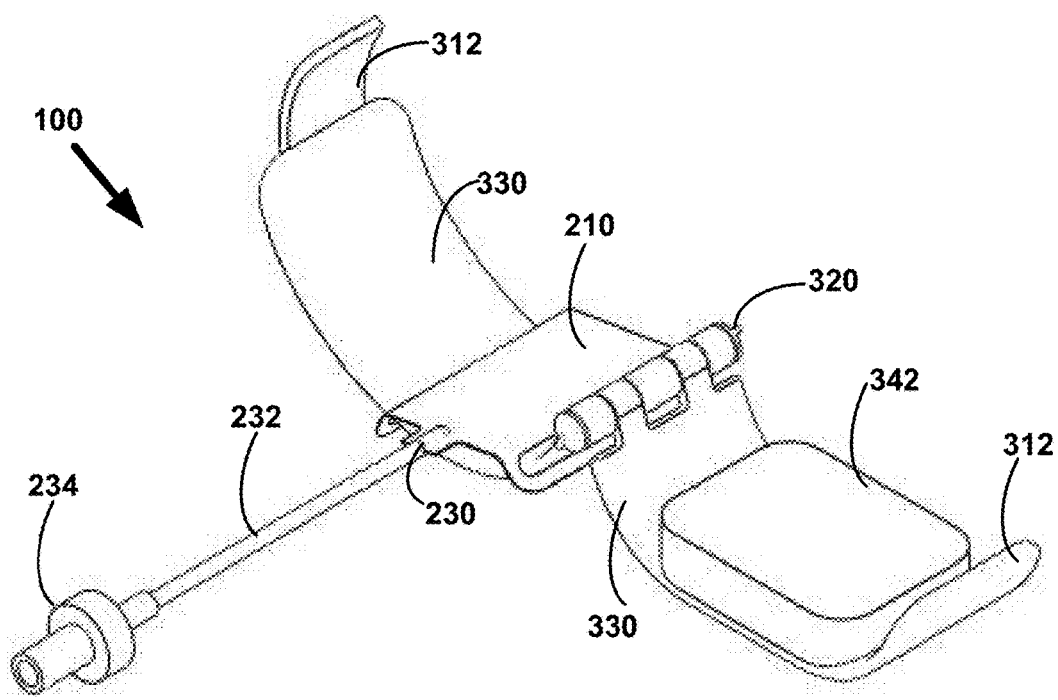
FIG. 4b is a diagram illustrating an example of a perspective view of a hemostasis band in an open state that is comprised of a balloon assembly and a band assembly.

FIG. 4b is a diagram illustrating an example of a perspective view of a hemostasis band 100 in an open state that is comprised of a balloon assembly 200 and a band assembly 300. The band 100 of FIG. 4b is essentially identical to FIG. 4a, except that the illustrations are taken from different points of view.

Figure 4C:
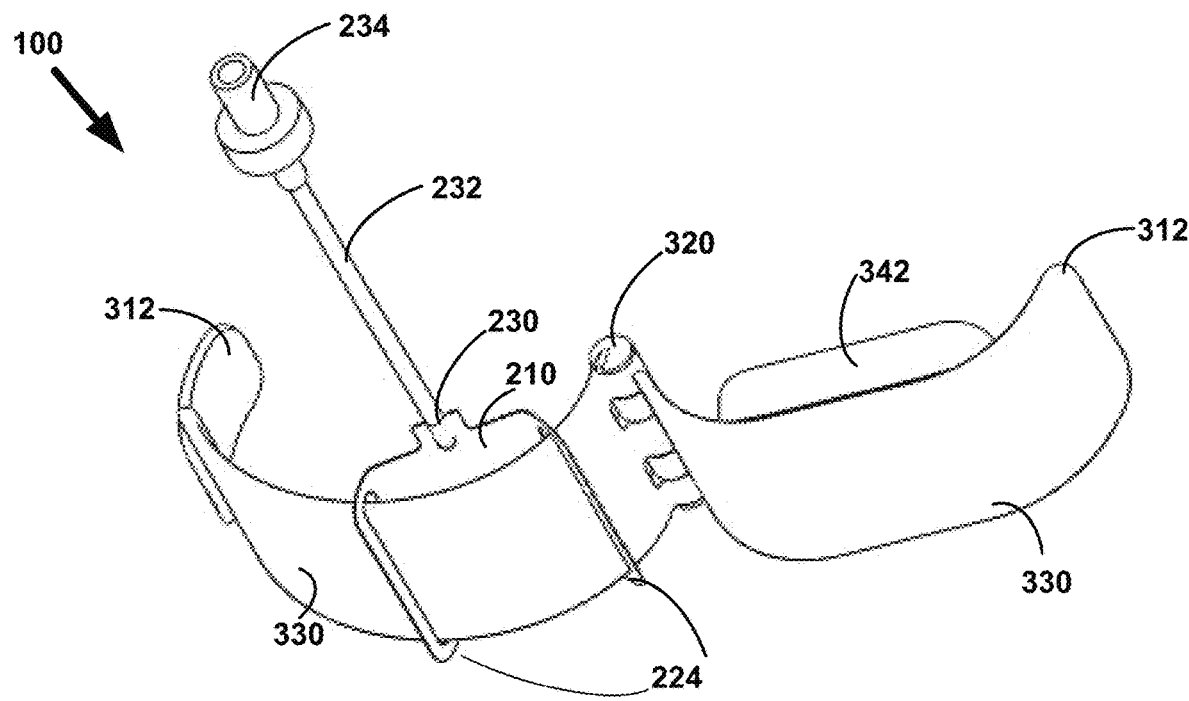
FIG. 4c is a diagram illustrating an example of a perspective view of a hemostasis band in an open state that is comprised of a balloon assembly and a band assembly.

FIG. 4c is a diagram illustrating an example of a perspective view of a hemostasis band 100 in an open state that is comprised of a balloon assembly 200 and a band assembly 300. The band 100 of FIG. 4c is substantially identical to the band 100 of FIGS. 4a and 4b, differing primarily in point of view. FIG. 4c illustrates the spatial relationship between the balloon 210, the two openings 220 of the balloon assembly 200, and the segment 330 positioned between the two openings 220.

Figure 4D:
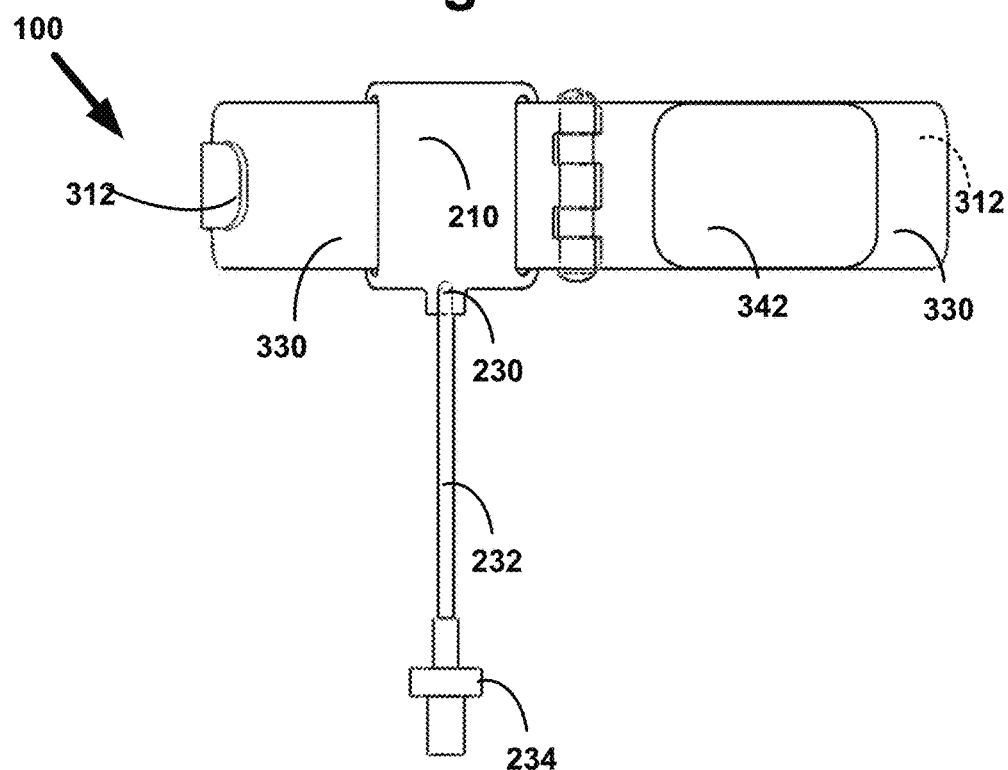
FIG. 4d is a diagram illustrating an example of a top view of a hemostasis band in an open state that is comprised of a balloon assembly and a band assembly.

FIG. 4d is a diagram illustrating an example of a top view of a hemostasis band 100 in an open state that is comprised of a balloon assembly 200 and a band assembly 300. The band 100 of FIG. 4d is substantially identical to the band 100 of FIGS. 4a-4c, differing primarily in point of view.

Figure 4E:
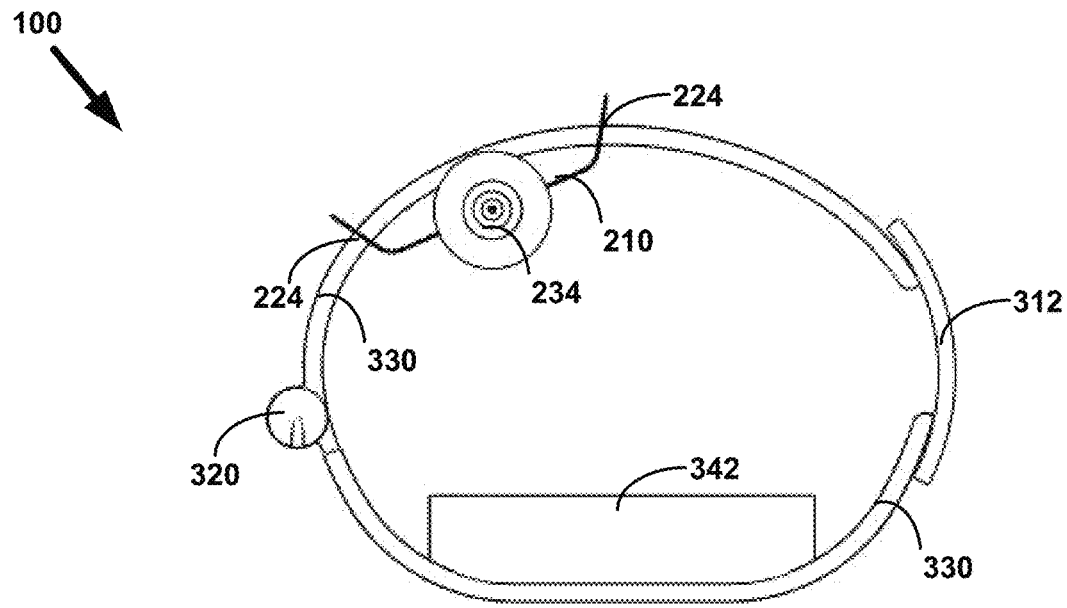
FIG. 4e is a diagram illustrating an example of a side view of a hemostasis band in a closed state that is comprised of a balloon assembly and a band assembly.

FIG. 4e is a diagram illustrating an example of a side view of a hemostasis band 100 in a closed state that is comprised of a balloon assembly 200 and a band assembly 300. FIG. 4e illustrates a closed band 100 where FIG. 4a illustrates an open band 100 from the same orientation.

Figure 4F:
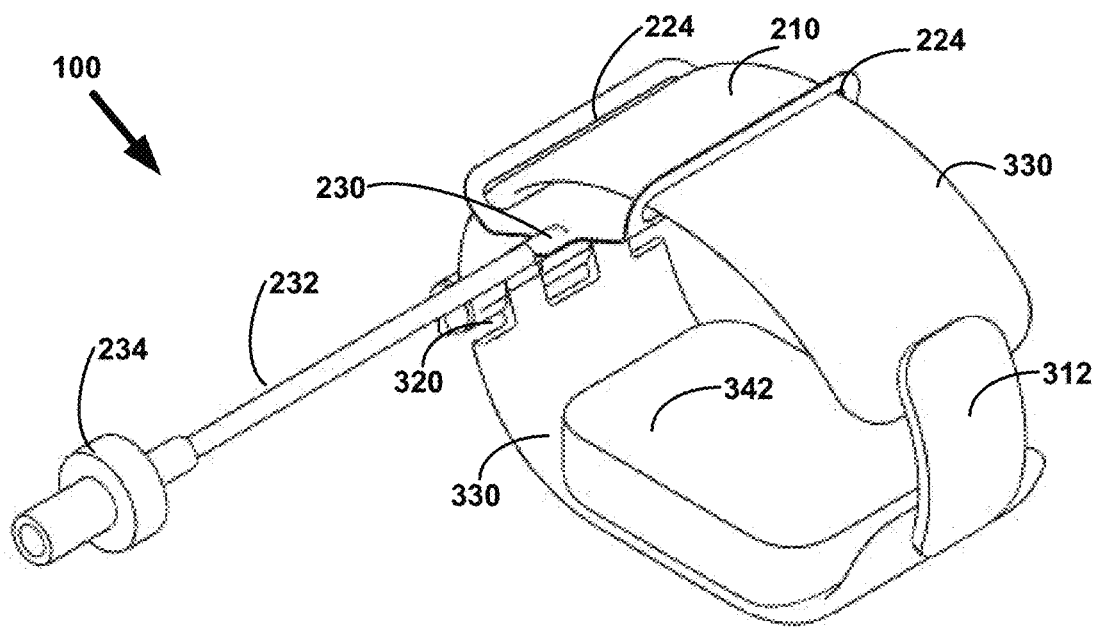
FIG. 4f is a diagram illustrating an example of a perspective view of a hemostasis band in a closed state that is comprised of a balloon assembly and a band assembly.

FIG. 4f is a diagram illustrating an example of a perspective view of a hemostasis band 100 in a closed state that is comprised of a balloon assembly 200 and a band assembly 300. FIG. 4f corresponds close to FIG. 4b, with the primary difference being in the operating state of the band 100.

V. Process Flow View

Figure 5:
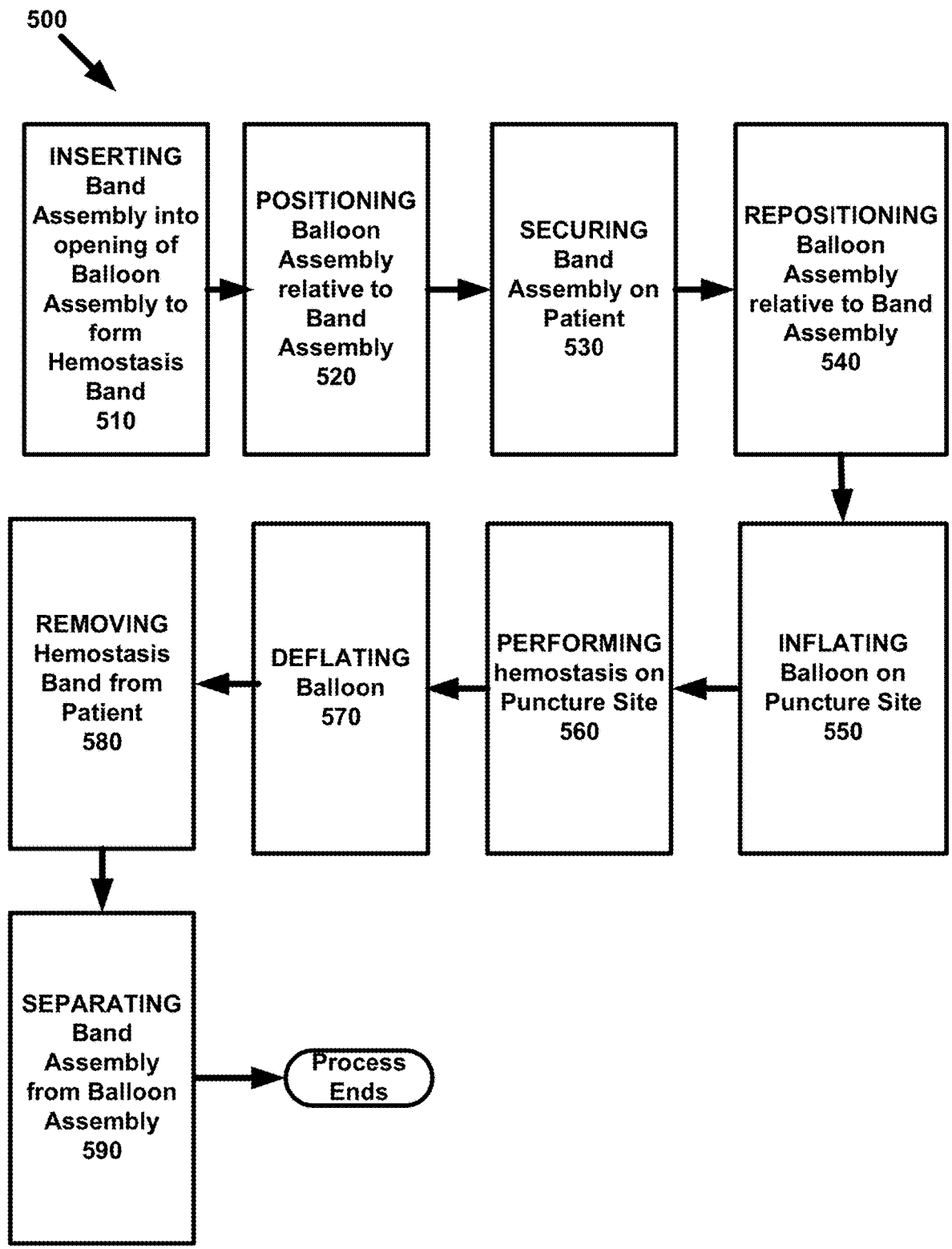
FIG. 5 is a flow chart diagram illustrating an example for using a hemostasis band that is comprised of a balloon assembly and a band assembly.

FIG. 5 is a flow chart diagram illustrating an example for using a hemostasis band 100 that is comprised of a balloon assembly 200 and a band assembly 300.

At 510, the band assembly 300 can be inserted into one or more openings 220 in the balloon assembly 200, securing in a non-permanent way, the combination forming the hemostasis band 100.

At 520, the balloon assembly 200 is positioned with respect to the band assembly 300. This is typically done by sliding the one or more openings 220 along one or more segments 330.

At 530, the band assembly 300 is secured on the patient 90, a process by which the band 100 is also secured on the patient 90. This process can include positioning the band 100 on the patient 90 and securing that position by closing the fastener components 310. In many instances of many embodiments, the balloon 210 will be positioned over the puncture site 89.

At 540, the balloon assembly 200 can be repositioned with respect to the band assembly 300 for the purposes of properly configuring and positioning the band 100 for providing hemostasis at the puncture site 89.

At 550, the one or more balloons 210 of the balloon assembly 200 are inflated. With embodiments involving a balloon pad 344, the balloon pad 344 can also be inflated at this time, or at a time prior to the inflating of the pressurizing balloon 210.

At 560, hemostasis is performed by the band 100, which can be adjusted as desired in terms of magnitude of pressure or the position of the balloon 210 or other component with direct contact to the puncture site 89.

At 570, the balloon 210 can be deflated. This can either be purposeful and active, or the end result of the balloons 210 inherent structure to slow leak air over a period of time.

At 580, the band can be removed from the patient 90. This is done by unfastening the fastener component 310 and removing the band 100 from the patient.

At 590, the balloon assembly 200 and the band assembly 300 can be separated from each other and disposed of, cleaned, etc. as appropriate.

The process is then complete.

VI. Glossary/Index

Table 1 below provides a chart of element numbers, element names, and element descriptions.

| Element Number | Name | Description |
|---|---|---|
| 89 | Puncture Site | A location on the patient 90 for which hemostasis is performed to prevent blood loss. In the context of catheterizations, the term "arteriotomy" is synonymous with the term "puncture site". |
| 90 | Patient | A living organism, typically a human being, subject to a hemostasis process. |
| 91 | Radial Artery | A blood vessel on a human patient 90 used to perform radial catheterization. The puncture site 89 for a radial catheterization procedure is a location on the Radial Artery 91 near a patient's 90 wrist. |
| 92 | Provider | A doctor, nurse, nurse practitioner, catheterization lab technician, physician assistant, paramedic, or other person involved in performing hemostasis on a patient 90. |
| 100 | Hemostasis Band | An apparatus formed when the band assembly 300 is inserted into one or more openings 220 in the balloon assembly 200. The hemostasis band 100 can be implemented using a variety of different materials including cloth, plastic, rubber, metal, steel, and ceramic. The hemostasis band 100 can also be referred to simply as the band 100. Some embodiments of the band 100 can be implemented such that the band is transparent or at least substantially transparent. This can aid providers 92 in preparing as well as monitoring the hemostasis process. In some embodiments of the band 100, the surfaces of the hemostasis band 100 that come into contact with the skin of a patient 90 can be coated with anti-adhesive coatings to prevent the band 100 from sticking to the skin of the patient 90. |
| 200 | Balloon Assembly | An assembly 200 that provides for combining with a band assembly 300 to form a hemostasis band 100. The balloon assembly 200 includes one or more openings 220 into which the band assembly 300 can be inserted into or connected through. The balloon assembly 200 can include at least one balloon 210, at least one opening 220 for the band assembly 300, and at least one inlet 230 for the inflation of the balloon 210. The balloon assembly 200 serves to pressurize the hemostasis band 100 after the band 100 is properly positioned on the patient 90. |
| 210 | Balloon | The balloon 210 can be the mechanism within the hemostasis band 100 by which pressure is placed on the puncture site 89. Balloons 210 are typically configured to be inflated with gasses such as air or liquids such as water, however balloons 210 can also be inflated with solid fluids such as gelatinous or substantially gelatinous materials. Balloons 210 can be comprised of a wide variety of materials, including but not limited to plastic, rubber, or latex. In many embodiments, it is the surface of the balloon 210 that comes into direct physical contact with the puncture site 89 of the patient 90. In many embodiments, the balloon 210 will be transparent or at least substantially transparent to permit the puncture site 89 to be seen by the provider 92 when (1) positioning the band 100 over the puncture site 89; (2) inflating the balloon 210; and (3) monitoring the hemostasis process after the balloon is inflated. |
| 212 | Window | Embodiments of balloon assembly 200 with an opaque balloon 210 may include a transparent or at least substantially transparent window 212 to permit the provider to see the puncture site 89 of the patient 90. |
| 220 | Opening | A space within the balloon assembly 200 that allows for the insertion of the band assembly 300 into the balloon assembly 200 and for the sliding of the balloon assembly |

-continued

| Element Number | Name | Description |
|---|---|---|
| | | 200 along the band assembly 300. Many embodiments of the balloon assembly 200 will include two openings 220, but the balloon assembly 200 can have as few as one opening 220 or as many as three or more openings 220. |
| 222 | Slits | A thin opening 220 with the thickness of a cut. Analogous to a button hole, a human being will often need to manually pry open a slit 222 before the band assembly 300 can be inserted. |
| 224 | Slots | An opening 220 that is wider than a slit 222. A slot 224 is a permanent opening that unlike a slit 222, is sustained without being manually pried open. |
| 226 | Members | A surface area or structure adjacent to a slot 224 that shapes the slot 224. Members 226 of all different shapes and sizes can be used to create an opening 220 of the desired shape and size. |
| 230 | Inlet | A pathway into the balloon 210 that allows for the inflation and deflation of the balloon 210. The inlet 230 of the balloon 210 may in some embodiments be filled with a tube 232. |
| 232 | Tube | A passageway to the inlet 230. Use of the tube 232 can permit the inflation and deflation of the balloon 210 to occur at a greater distance from the surface of the balloon 210. The tube 232 can also make it easier for a valve 234 to be used as part of the balloon assembly 200. In some embodiments, the tube 232 is a separate and distinct component of the balloon assembly 200. In other embodiments, the tube 232 can simply be the neck of the balloon 210. The structure and functionality of the tube 232 can be achieved using a balloon 210 with a similarly structured neck. |
| 234 | Valve | A device that can be included in the balloon assembly 200 that can control the flow into and out of the balloon 210. A typical valve will have at least two operating states, an operating state of being closed/sealed and an operating state of being open/unsealed. Some embodiments of the valve 234 may operate in a linear fashion between the two extreme states of totally closed/totally sealed and totally open/totally unsealed. Valves 234 can be made up of a wide variety of different materials, including but not limited to metal, rubber, plastic, and ceramic. Some valves 234 can include a pressure sensor. |
| 250 | Sheath | A cover for some or all of the balloon assembly 200. For example, the balloon 210, openings 220, and inlet 230 can each be integrated into a single sheath 250 that prevents the individual removal of any of the integrated components. |
| 300 | Band Assembly | An assembly 300 that provides for combining with a balloon assembly 200 to form a hemostasis band 100. In many embodiments, the band assembly 300 is removable from the balloon assembly 200 and it is the band assembly 300 which serves to secure the hemostasis band 100 on the puncture site 89 of the patient 90. In some embodiments, some portion of the band assembly 300 comes into direct contact with the puncture site 89, although it many embodiments it is the balloon 210 of the balloon assembly 200 that is intended to come into direct contact with the puncture site 89 on the patient 90. |
| 310 | Fastener Component | A mechanism or component of the band assembly 300 by which the band assembly 300 and the hemostasis band 100 as a whole, can be secured to the patient 90. Many embodiments of the band assembly 300 will require some type of fastener component 310. In some embodiments of the band assembly 300, the segment 330 of the assembly 300 is an elastic band that serves at its own fastener to the patient 90. In other embodiments, the band assembly 300 will use a snap, button, zipper, adhesive surface, hook and loop fastener 312, or other similar technology to secure two ends of the band assembly 300 together while the balloon assembly 200 is secured to the band assembly 300. |
| 312 | Hook and Loop Fastener | A type of fastener made out of two strips of VELCO ® material. |
| 320 | Hinge | A joint that links one segment 330 of the band assembly to another segment 330. The hinge 320 permits relative movement between the two or more segments 330. |

| Element Number | Name | Description |
|---|---|---|
| 330 | Segment | A surface on the band assembly 300 that can also be referred to as the "band" of the band assembly 300. Many embodiments of the band assembly 300 will include two segments 330 joined by a hinge 320, although some alternative embodiments can include as few as one segment 330 (an elastic loop for example) or more than two segments 330. Segments 330 can be flexible, rigid, or partially rigid/partially flexible. Many embodiments of rigid or at least partially rigid segments 330 will involve curved segments 330. Examples of segments 330 can include a flexible elastic band, a strip, a loop, a semi-flexible/semi-rigid band, and a fully rigid band. Segments 330 can also be referred to as "body components" 330 as segments serve as the relevant surface of the band assembly 300 that various components are attached to (virtually all of the components of the band assembly 300) as well as the relevant portion of the band assembly 300 that moves within the openings 220 and with respect to the balloon assembly 200. |
| 332 | Curved Segment | A segment 330 that is at least semi-rigid such that it can maintain an at least somewhat curved shape. |
| 340 | Padding Component | A mechanism to enhance the comfort of the patient 90 with respect to the apparatus 100 and the band assembly 300. Examples of padding components include a foam pad 342, a second balloon, and other types of active or passive padding materials. |
| 342 | Foam Pad | An example of a padding component 340 |
| 344 | Balloon Pad | An example of a padding component 340. |

VII. Alternative Embodiments

No patent application can disclose all of the potential embodiments of an invention. In accordance with the provisions of the patent statutes, the principles and modes of operation of the balloon assembly 200, the band assembly 300, the aggregate hemostasis band 100, and the method 500 of use thereof are explained and illustrated in certain preferred embodiments. However, it must be understood that the hemostasis band 100, balloon assembly 200, band assembly 300, and method 500 of their use may be practiced otherwise than is specifically explained and illustrated without departing from its spirit or scope. Each of the various elements described in the index above can be implemented in a variety of different ways while still being consistent with the spirit and scope of the invention. For example, a hemostasis band 100 comprised of the balloon assembly 200 and the band assembly 300 can be implemented in far more different ways using far more different components in far more different configurations than what is illustrated in the accompanying figures.

The description of the apparatus provided above should be understood to include all novel and non-obvious combination of elements described therein, and claims may be presented in this or a later application to any novel non-obvious combination of these elements. Moreover, the foregoing embodiments are illustrative, and no single feature or element is essential to all possible combinations that may be claimed in this or a later application.

The invention claimed is:

1. A hemostasis band, comprising:
a sheath;
a balloon positioned inside the sheath;
a band assembly, wherein the band assembly includes first and second segments connected by a hinge such that the first and second segments are movable relative to one another;
at least one opening in the sheath that is configured to receive the first segment of the band assembly;
an inlet that provides for the inflation of said balloon; and
a pad arranged on the second segment of the band assembly.

2. The hemostasis band of claim 1, wherein the at least one opening includes two openings, and the two openings are slots.

3. The hemostasis band of claim 1, further comprising at least one member configured to shape a space of the at least one opening.

4. The hemostasis band of claim 3, wherein the at least one member is integral to the sheath.

5. The hemostasis band of claim 1, wherein the balloon and the sheath are at least substantially transparent.

6. The hemostasis band of claim 1, wherein the sheath and the balloon include a window, and the window is at least substantially transparent.

7. The hemostasis band of claim 1, wherein the band assembly is configured to secure the hemostasis band onto a wound site of a patient.

8. The hemostasis band of claim 1, wherein the band assembly includes a fastener configured to secure the band assembly to a patient.

9. The hemostasis band of claim 8, wherein the fastener includes a hook and loop fastener.

10. The hemostasis band of claim 1, wherein the balloon is integral with the sheath.

11. The hemostasis band of claim 1, wherein the inlet is integral with the sheath.

12. The hemostasis band of claim 1, wherein the balloon and inlet are integral with the sheath.

13. The hemostasis band of claim 1, wherein the at least one opening is configured to reversibly receive the first segment of the band assembly.

* * * * *